(12) United States Patent
Lee et al.

(10) Patent No.: US 7,956,755 B2
(45) Date of Patent: Jun. 7, 2011

(54) APPARATUS AND/OR METHOD FOR INDUCING SOUND SLEEP AND WAKING

(75) Inventors: Mi-hee Lee, Yongin-si (KR); Seok-won Bang, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 520 days.

(21) Appl. No.: 11/513,080

(22) Filed: Aug. 31, 2006

(65) Prior Publication Data

US 2007/0083079 A1   Apr. 12, 2007

(30) Foreign Application Priority Data

Oct. 7, 2005   (KR) .................. 10-2005-0094538

(51) Int. Cl.
*G08B 23/00* (2006.01)
(52) U.S. Cl. .................... 340/575; 340/573.1
(58) Field of Classification Search .......... 340/575, 340/573.1, 56; 600/26, 538–9
See application file for complete search history.

(56) References Cited

U.S. PATENT DOCUMENTS

| | | | |
|---|---|---|---|
| 2004/0103475 A1* | 6/2004 | Ogawa et al. .............. | 5/613 |
| 2005/0115561 A1* | 6/2005 | Stahmann et al. ....... | 128/200.24 |
| 2005/0143617 A1* | 6/2005 | Auphan ..................... | 600/26 |
| 2006/0040739 A1* | 2/2006 | Wells ........................ | 463/37 |

FOREIGN PATENT DOCUMENTS

| | | |
|---|---|---|
| JP | 04-052901 | 2/1992 |
| JP | 05-0146512 | 6/1993 |
| JP | 07-059757 | 3/1995 |
| JP | 2000-083927 | 3/2000 |
| JP | 2001-017550 | 1/2001 |
| JP | 2003-260040 | 9/2003 |
| JP | 2003-339674 | 12/2003 |
| JP | 2005-21331 | 1/2005 |
| JP | 2005-177158 | 7/2005 |
| KR | 2003-0032529 | 4/2003 |

OTHER PUBLICATIONS

Japanese Office Action dated Sep. 8, 2009, issued in corresponding Japanese Patent Application No. 2006-270356.

* cited by examiner

*Primary Examiner* — Shirley Lu
(74) *Attorney, Agent, or Firm* — Staas & Halsey LLP

(57) ABSTRACT

Disclosed herein are a method and apparatus to induce sound sleep and waking, selecting a protocol to control a sound sleep and waking environment depending on a sleep type selected by a user; adjusting the sleep environment of the user according to the selected protocol; determining a sleep state of the user by measuring physiological signals of the user during sleep in the sleep environment using a sensor which does not contact a body of the user; detecting variation in the physiological signals of the user; and re-adjusting the sleep environment by changing parameters of the protocol depending on the detected variation in the physiological signals. As a result, there is an advantage in that it is possible to naturally induce sound sleep and waking.

17 Claims, 5 Drawing Sheets

FIG. 5

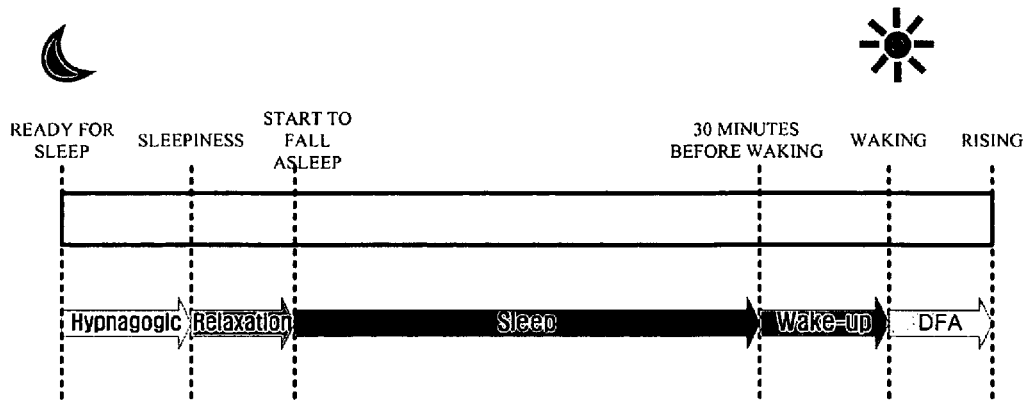

FIG. 6

| four sleep stages | Hypnagogic | Relaxation | Sleep | Wake-up |
|---|---|---|---|---|
| sound (quiet environment) | Turning up sedative music Brainwave inducing sound | Fading natural sound | No operation | Turning-up light music |
| sound (noisy environment) | White noise | Turning-down white noise | White noise | Turning-up light music |
| light | Gradual dimming of soft light : light become gradually dark from below 150 lux of illumination 30 minutes before falling asleep | Slow light fluctuation : light flickers four times at constant interval and once at long interval to induce deep breathing | Dim light : light is kept dim | Refreshing light : ambient light gradually become bright using indirect lighting 30 minutes before waking and, when wake-up time is reached, light from natural light and a fluorescent lamp is kept at 1000 lux of illumination |
| temperature (cold drafton face) | start of cold draft ($\Delta_{CBT} \approx -0.3°C/10min$) | cold draft until DPG=0 | No operation | No operation |
| temperature (mat heating) | Foot heating ($\Delta_{FT} \approx 4°C/10min$) | Foot heating until DPG=0 | No operation | Body heating ($\Delta_{CBT} \approx 0.1°C/30min$) |
| aroma | start of aroma generation (chrysanthemum, marjoram, honey dream, lavender, hamomile) | maintenance of aroma | No operation | aroma generation |
| humidity | start of control for appropriate humidity(50%+/-5%) | maintenance of appropriate humidity | maintenance of appropriate humidity | maintenance of appropriate humidity |
| oxygen | start of oxygen generation(25%) | maintenance of appropriate amount of oxygen | maintenance of appropriate amount of oxygen | maintenance of appropriate amount of oxygen |
| massage | decrease of inclination | maintenance of horizontality | maintenance of horizontality | increase of inclination |
| | start of air massage | maintenance of air massage | No operation | start of air massage |

APPARATUS AND/OR METHOD FOR INDUCING SOUND SLEEP AND WAKING

CROSS-REFERENCE TO RELATED APPLICATION

This application claims priority from Korean Patent Application No. 10-2005-0094538 filed on Oct. 7, 2005 in the Korean Intellectual Property Office, the disclosure of which is incorporated herein by reference in its entirety.

BACKGROUND OF THE INVENTION

1. Field of the Invention

The present invention relates generally to a method and apparatus to induce sound sleep and waking, and, more particularly, to a method and apparatus to induce sound sleep and waking, which measure physiological signals using a non-contact type sensor which does not contact the body of a user, and, when variation in the measured physiological signals occurs, re-adjusts the sleep environment by changing a sound sleep and waking inducing protocol, thereby enabling the feedback control of the sleep environment.

2. Description of the Related Art

Due to the complicated lifestyle in modern societies and the influence between the members of the societies, modern people are subject to a lot of stress. Because of the stress, they do not have sufficient sleep, which undesirably affects their bodies. Therefore, in order to induce comfortable and agreeable sleep, a number of technologies have been proposed.

Korean Unexamined Patent Publication No. 2003-0032529 discloses a device and method to induce sleep, which output vibrations and/or ultrasound waves in a frequency band, which was determined in repeated studies, depending on the body state of a user while collecting physiological information about the user, thereby optimally inducing sleep.

Furthermore, Japanese Unexamined Patent Publication No. 2003-260040 discloses a sleeping depth estimation device that includes a vital information sensor detecting vital information including the heart rate and breathing rate of a human body, a vital information processing circuit calculating a plurality of pieces of basic data about sleep depth through the processing of the vital information detected by the vital information sensor, and a sleep depth estimating circuit estimating the sleep depth based on the basic data obtained by the vital information processing circuit.

However, the related art technologies have problems in that a sensor detecting the sleep state of a user is not used, or, even if a sensor is used, the sensor contacts the body of the user, so that a user, who is trying to fall asleep, feels uncomfortable. Furthermore, there is a problem in that it is hard to simultaneously detect variation in the physiological signals of a sleeping user and variation in the sleep environment, and perform feedback control on the sleep environment even if a non-contact type sensor is used.

SUMMARY OF THE INVENTION

Additional aspects and/or advantages of the invention will be set forth in part in the description which follows and, in part, will be apparent from the description, or may be learned by practice of the invention.

Accordingly, the present invention has been made keeping in mind the above problems occurring in the related art, and an aspect of the present invention provides an apparatus and method to induce sound sleep and waking, which measure physiological signals of a user during sleep using a non-contact type sensor and, at the same time, control the sleep environment, thereby enabling the feedback control of the induction of sound sleep and waking.

The objects of the present invention are not limited to the above object, and objects not described will be understood by those skilled in the art from the following description.

According to an aspect of the present invention, an apparatus is provided to induce sound sleep and waking, including an input unit to receive a sleep type from a user; a protocol selection unit to select a protocol to control an environment for sound sleep and waking depending on the received sleep type; a sleep environment adjustment unit to adjust a sleep environment of the user according to the selected protocol; a sleep state determination unit to determine a sleep state of the user by measuring physiological signals of the user during sleep in the sleep environment using a sensor that does not contact a body of the user; and a physiological signal variation detection unit to detect variation in the physiological signals of the user using the determined sleep state; wherein, when the variation in the physiological signals is detected by the physiological signal variation detection unit, the sleep environment adjustment unit re-adjusts the sleep environment by changing one or more parameters of the protocol depending on the variation is provided.

Furthermore, an aspect of the present invention provides a method of inducing sound sleep and waking, including selecting a protocol to control a sound sleep and waking environment depending on a sleep type selected by a user; adjusting the sleep environment of the user according to the selected protocol; determining a sleep state of the user by measuring physiological signals of the user during sleep in the sleep environment using a sensor which does not contact a body of the user; detecting variation in the physiological signals of the user; and re-adjusting the sleep environment by changing parameters of the protocol depending on the detected variation in the physiological signals.

BRIEF DESCRIPTION OF THE DRAWINGS

The above and/or other objects, features and advantages of the present invention will be more clearly understood from the following detailed description taken in conjunction with the accompanying drawings, in which:

FIG. 5 is a diagram illustrating sleep stages from a sleep onset time to a wake-up time in the method of inducing sound sleep and waking according to the embodiment of the present invention;

FIG. 6 is a diagram illustrating a method of adjusting the sleep environment for each of the sleep stages as a table in the method of inducing sound sleep and waking according to the embodiment of the present invention.

DETAILED DESCRIPTION OF THE PREFERRED EMBODIMENTS

Figure 1:
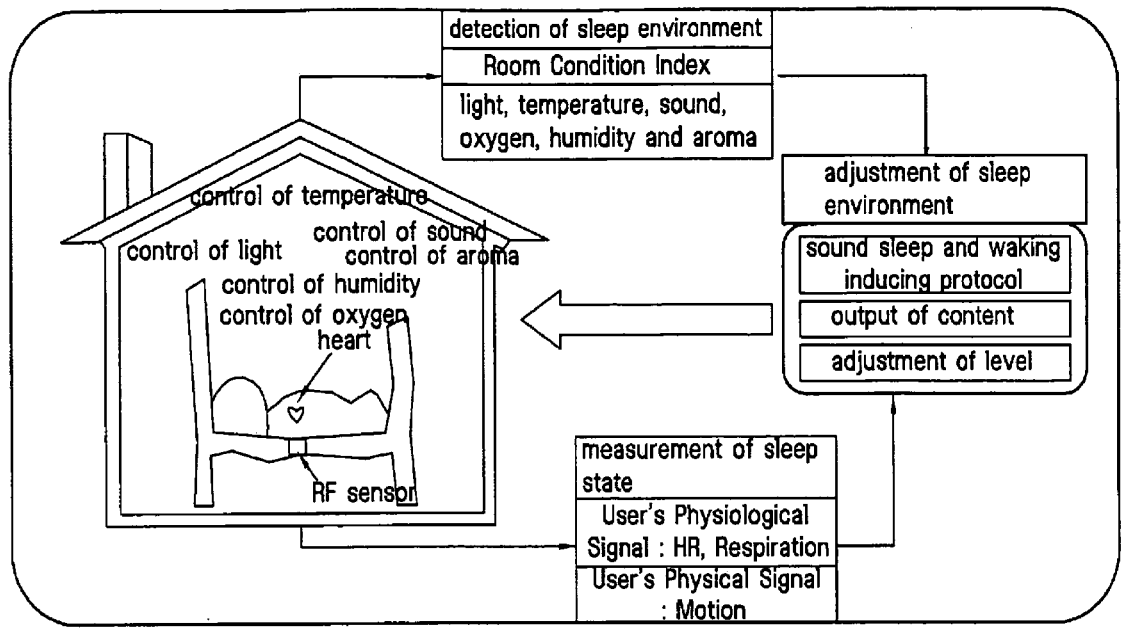
FIG. 1 is a diagram illustrating the operational concept of an apparatus to induce sound sleep and waking according to an embodiment of the present invention.

Reference will now be made in detail to the embodiments of the present invention, examples of which are illustrated in the accompanying drawings, wherein like reference numerals refer to the like elements throughout. The embodiments are described below to explain the present invention by referring to the figures.

FIG. 1 is a diagram schematically illustrating the operational principle of an apparatus to induce sound sleep and waking according to an embodiment of the present invention. As illustrated in FIG. 1, a non-contact type sensor is mounted in a bed, the wall of a bedroom, or an electronic product in the vicinity of a sleeping user, measures physiological signals, such as heart rate, heart rate variability, and respiratory rate, from heart beat and respiration and additionally senses the movement of the user in the sleep state. Thereafter, the sleep state of the user is analyzed based on the measurement and the sensing. In this case, the heart rate variability includes High Frequency (HF) rate and Low Frequency (LF) rate obtained through the analysis of the heart rate.

Furthermore, the sleep environment, such as the temperature, humidity, sound, oxygen, or aroma, surrounding the bed of a user is measured and analyzed. Using the analyzed sleep state and sleep environment, the sleep state and sleep environment of the user are controlled; this is performed by selecting protocol parameters to induce proper sound sleep and waking and appropriately changing the parameters depending on the environment. In this case, the protocol parameters are described in detail in a description of a protocol selection unit 120, which will be given below.

It will be understood that each block and each operation of the flowchart illustrations, and combinations of blocks and operations in the flowchart illustrations, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means to implement the functions specified in the flowchart block or blocks, or the flowchart operations and operations.

These computer program instructions may also be stored in a computer usable or computer-readable memory that can direct a computer or other programmable data processing apparatus to function in a particular manner, such that the instructions stored in the computer usable or computer-readable memory produce an article of manufacture including instruction means that implement the function specified in the flowchart block or blocks or the flowchart operation and operations.

The computer program instructions may also be loaded onto a computer or other programmable data processing apparatus to cause a series of operations to be performed on the computer or other programmable apparatus to produce a computer implemented process such that the instructions that execute on the computer or other programmable apparatus provide operations to implement the functions specified in the flowchart block or blocks or the flowchart operation and operations.

Further, each block of the flowchart illustrations may represent a module, segment, or portion of code, which comprises one or more executable instructions to implement the specified logical function(s). It should also be noted that in some alternative implementations, the functions noted in the blocks and the operations may occur in a different order. For example, two blocks or two operations shown in succession may in fact be executed substantially concurrently, or the blocks and the operations may sometimes be executed in the reverse order, depending upon the functionality involved.

Figure 2:
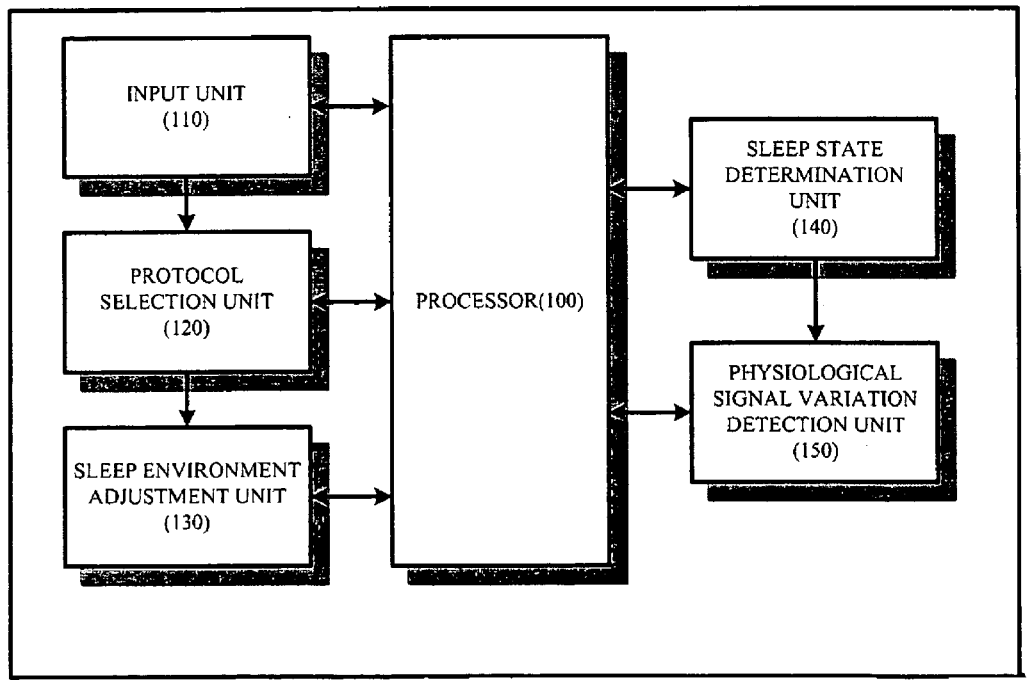
FIG. 2 is a diagram illustrating the construction of the apparatus to induce sound sleep and waking according to the embodiment of the present invention.

FIG. 2 is a diagram illustrating an apparatus to induce sound sleep and waking according to an embodiment of the present invention. Referring to FIG. 2, the apparatus to induce sound sleep and waking includes an input unit 110, a protocol selection unit 120, a sleep environment adjustment unit 130, a sleep state determination unit 140, and a physiological signal variation detection unit 150.

The input unit 110 receives a sleep type input from a user. When a wake-up time is input by the user with respect to the sleep onset time of the user, a sleep time and total sleep duration are calculated and then the type of sleep is determined. As a result, the sleep type is determined based on factors associated with a sleep time, sleep duration and/or sleep depth.

The protocol selection unit 120 selects a protocol to induce sound sleep and waking, which controls a sound sleep and waking environment depending on the input sleep type. In this case, the parameters of the protocol are created by audio and/or video content and a level representing information about the state of the external environment of a sleep space. The level is adjusted based on at least one of light, oxygen, temperature, humidity, aroma or sound for each of sleep stages from the sleep onset time to the wake-up time of the user. In this case, the sleep stages are the division of a period from a sleep onset time to a wake-up time according to sleep depth in the method of inducing sound sleep and waking according to the embodiment of the present invention, which are illustrated in FIG. 5.

FIG. 5 is a diagram illustrating sleep stages from a sleep onset time to a wake-up time in the method of inducing sound sleep and waking according to the embodiment of the present invention. The sleep stages are described referring to FIG. 5. The sleep stages include a total of four stages: a hypnagogic stage spanning from lying in bed to immediately before feeling sleepy, a relaxation stage spanning from feeling sleepy to immediately before falling asleep, a sleep stage spanning from falling asleep to immediately before finally inducing waking, and a wake-up stage spanning from starting to wake up to finally waking up.

Meanwhile, the sleep environment adjustment unit 130 adjusts the sleep environment of a user according to the selected protocol to induce sound sleep and waking. According to the selected protocol to induce sound sleep and waking, the sleep environment unit 130 varies the level values of the protocol by controlling one or more of an Audio-Video (AV) device, a lighting device, an oxygen generation device, a temperature control device, a humidity control device, a aroma generation device and a sound output device, thereby adjusting the sleep environment of the user.

The sleep stage determination unit 140 measures the physiological signals of a user during sleep in the sleep environment and then determine the sleep state of the user. In this case, according to an aspect of the present invention, it is understood that the physiological signals can be measured based on heart rate, heart rate variability and/or respiratory rate, which are derived from heart beat and respiration as main indicators although there are various phenomena, based on which the sleep state of the user can be determined, such as heart rate, blood pressure, brain waves, electrocardiogram, temperature, perspiration, pulse and respiration. Therefore, the sleep state can be determined based on whether the indicators stay the same, increase, or decrease by comparing the indicators with a physiological signal variation model that may be a reference. For example, if gamma waves or beta waves, which are types of brain waves generated when a human is awake, are detected in the sleep stage, or the heart rate or respiratory rate suddenly increases, it is determined that the sleep stage may be unstable.

Furthermore, it is understood that the sleep state determination unit 140 can measure physiological signals using a Doppler radar sensor which is located within a distance of three meters from the heart of the user but does not contact the body of the user. It is experimentally known that when the Doppler radar sensor is used, 90% or more accuracy is exhibited within a distance of three meters from the heart of the user. The Doppler radar sensor is based on a Doppler shift principle, in which frequency varies depending on variation in locations of an object and an observer, and can acquire heart rate, heart rate variation and respiratory rate information using the variation of the difference between Doppler frequencies of signals reflected by the chest movement of a user during sleep.

Figure 3:
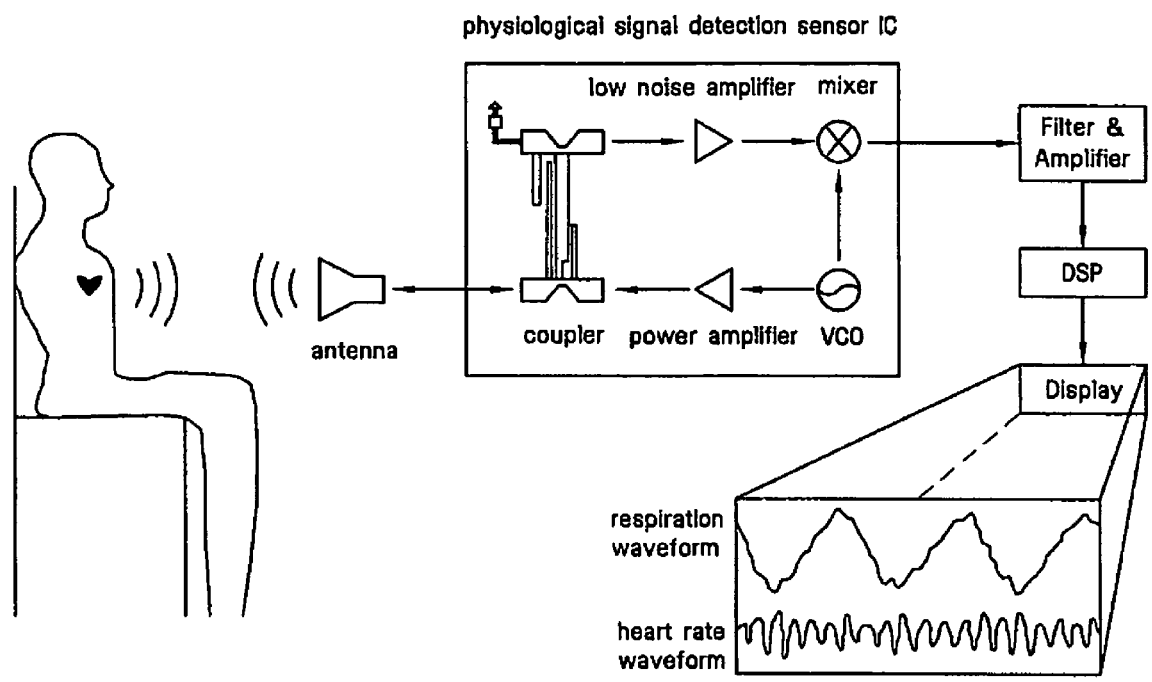
FIG. 3 is a diagram illustrating a concept of remotely measuring physiological signals in the apparatus to induce sound sleep and waking according to an embodiment of the present invention.

FIG. 3 is a diagram illustrating the measuring process, and illustrates remotely measuring physiological signals in the apparatus to induce sound sleep and waking according to an aspect of the present invention. Referring to FIG. 3, mixed signals detected through a physiological signal detection sensor Integrated Circuit (IC), which includes a coupler, a low-noise amplifier, a mixer, a power amplifier and a Voltage Controlled Oscillator (VCO), are filtered through a filter, amplified through an amplifier, processed through a Digital Signal Processor (DSP), and then output through a display device. In FIG. 3, it is known that respiration waveforms and heart rate waveforms are output. It has already been described that heart rate, heart rate variability and respiratory rate are measured based on the respiration waveforms and heart rate waveforms.

Meanwhile, the sleep state determination unit 140 determines the sleep state thereof by measuring the behavior of a user during sleep. Sleep behavior includes, for example, the behavior of tossing, turning, and snoring. However, it is understood that the sleep behavior can be processed as a dependent element, compared to physiological signals.

The physiological signal variation detection unit 150 detects variation in the physiological signals of a user using the determined sleep state. In particular, the physiological signal variation detection unit 150 determines the sleep state of a user based on whether heart rate, heart rate variability and respiratory rate, which are derived from the heart beat and respiration of the user, are increasing, according to a physiological signal variation model for each of the well-known sleep stages of a human, and compares the increase and decrease of the indications with the increase and decrease of those of the model, thereby detecting variation in physiological signals according to the sleep stages of the user, which will be described with reference to FIG. 4.

Meanwhile, when predetermined variation in the physiological signals is detected by the physiological signal variation detection unit 150, the sleep environment adjustment unit 130 performs to feedback control by varying the protocol to induce sound sleep and waking depending on the variation, and re-adjusting the sleep environment of the user.

The processor 100 controls input unit 100, protocol selection unit 120, sleep environment adjustment unit 130, sleep state determination unit 140, and physiological signal variation detection unit 150 and also controls the sleep environment through feedback.

Figure 4:
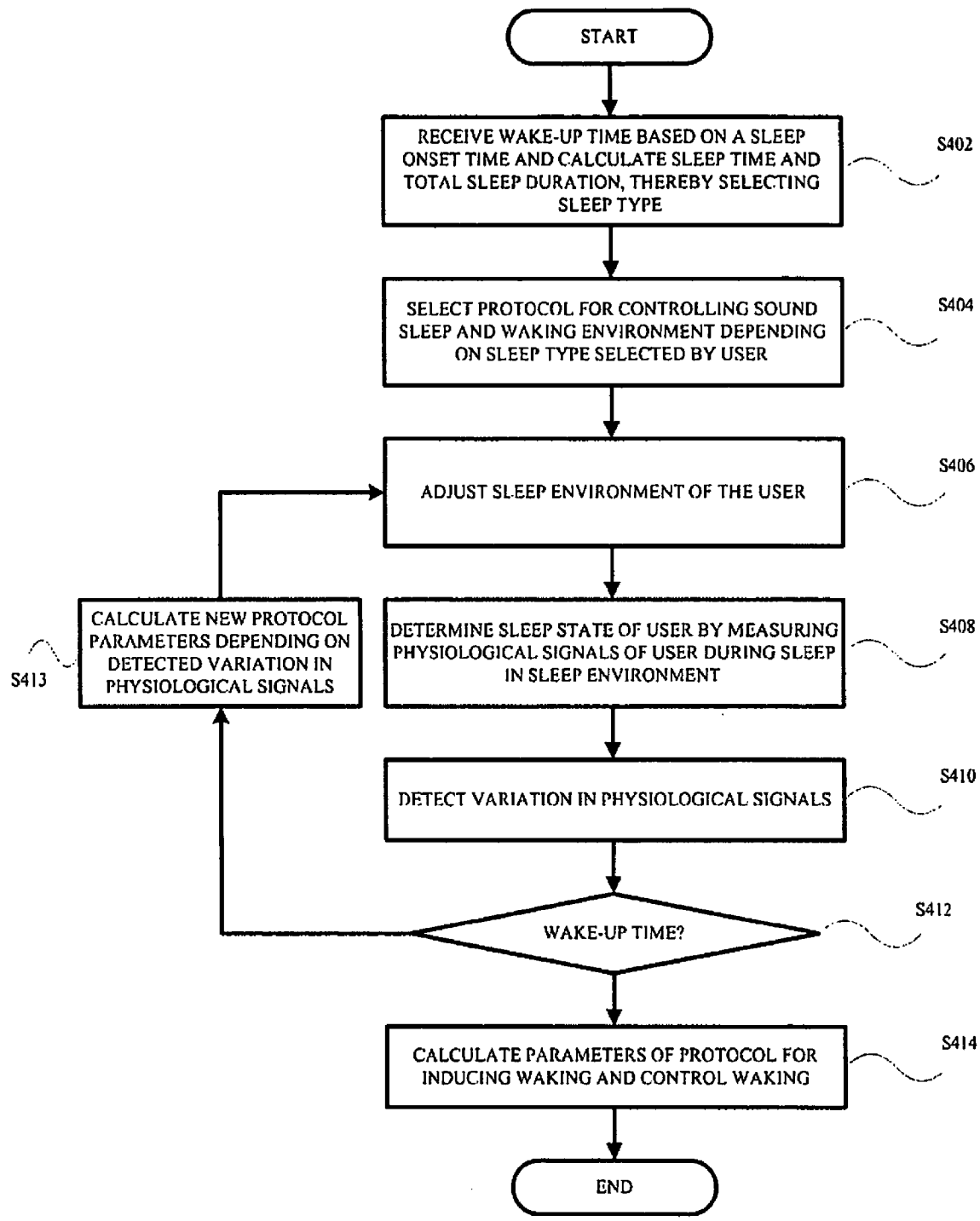
FIG. 4 is a flowchart illustrating a method of inducing sound sleep and waking according to an embodiment of the present invention.

Hereinafter, a method of inducing sound sleep and waking is described with reference to FIG. 4. FIG. 4 is a diagram illustrating the flowchart of the method of inducing sound sleep and waking according to an embodiment of the present invention.

First, when a user inputs a wake-up time based on a sleep onset time, the input unit 110 receives the wake-up time, calculates the a sleep time and total sleep duration, and automatically selects a sleep type at operation S402. The protocol selection unit 120 selects a protocol to control a sound sleep and waking environment depending on the sleep type selected by the user at operation S404.

As described above, the parameters of the protocol includes levels representing content, including audio and video, and information about the states of the external environment of a sleep space, the levels referring to values controlled by the amounts of light and oxygen, temperature, humidity, aroma or sound for each of the sleep stages of sleep duration from the sleep onset time to the wake-up time.

According to the protocol for inducing sound sleep and waking selected as described above, the sleep environment unit 130 adjusts the sleep environment of the user at operation S406. In particular, the sleep environment unit 130 adjusts the sleep environment of the user by controlling any one of an AV device, a lighting device, an oxygen generation device, a temperature control device, a humidity control device, an aroma generation device and a sound output device.

Meanwhile, the sleep state determination unit 140 determines the sleep state of the user by measuring the physiological signals of the user during sleep in the sleep environment using the non-contact type sensor at operation S408. It is understood that the physiological signals can be measured through indicators including the heart rate, heart rate variability and respiratory rate, which are calculated from the heartbeat and respiration of the user. In this case, the sleep state of the user can be determined depending on whether the indicators are maintained, increase or decrease. In addition, the sleep state of the user may be determined by measuring the movement during sleep, such as the tossing and turning of the user. Using the determined sleep state, the physiological signal variation detection unit 150 detects variation in the physiological signals including the heart rate, heart rate variability and respiratory rate of the user at operation S410.

The detection of variation in physiological signals is performed using a Doppler radar sensor. As long as the sensor is located within a distance of three meters from the heart of the user and does not contact the body of the user, it is mounted in the inner wall of a bedroom, a bed, or in a home appliance.

Meanwhile, the detection of variation in physiological signals can be performed by comparing whether indicators, such as heart rate, heart rate variability and respiratory rate, which are derived from heart beat and respiration, are maintained, increase, or decrease with the model according to the physiological signal variation model for each of the sleep stages of a human.

For instance, according to the physiological signal variation model for each of the well-known sleep stages of a human, if, in a sleep stage, reference values indicate that there is no variation in heart rate, heart rate variability decreases, and the respiratory rate is maintained, and measured values indicate that the heart rate increases, the heart rate variability decreases, and respiratory rate increases, a stimulus which can adjust the heart rate, the heart rate variability and the respiratory rate to reference values is required. Therefore, the processor 100 selects protocol parameters to decrease the heart rate, maintaining the respiratory rate and decreasing the respiratory rate, and controls the sleep environment adjustment unit 130 so as to adjust temperature, humidity, light, oxygen, sound and/or aroma commensurate with the protocol parameters. In this case, the physiological signal variation model for of the respective the well-known sleep stages of humans is a well-known model, so that a detailed description thereof is omitted here.

Meanwhile, the processor 100 determines whether the wake-up time is reached at operation S412, and, if the wake-up time is not reached, calculates the protocol parameters depending on the detected variation in the physiological signals at operation S413 and then performs feedback control by re-adjusting the sleep environment of the user based on the calculated protocol one or more parameters at operation S406. If the wake-up time is reached, the processor 100 calculates protocol parameters to induce waking and then induces waking at operation S414.

Figure 7:
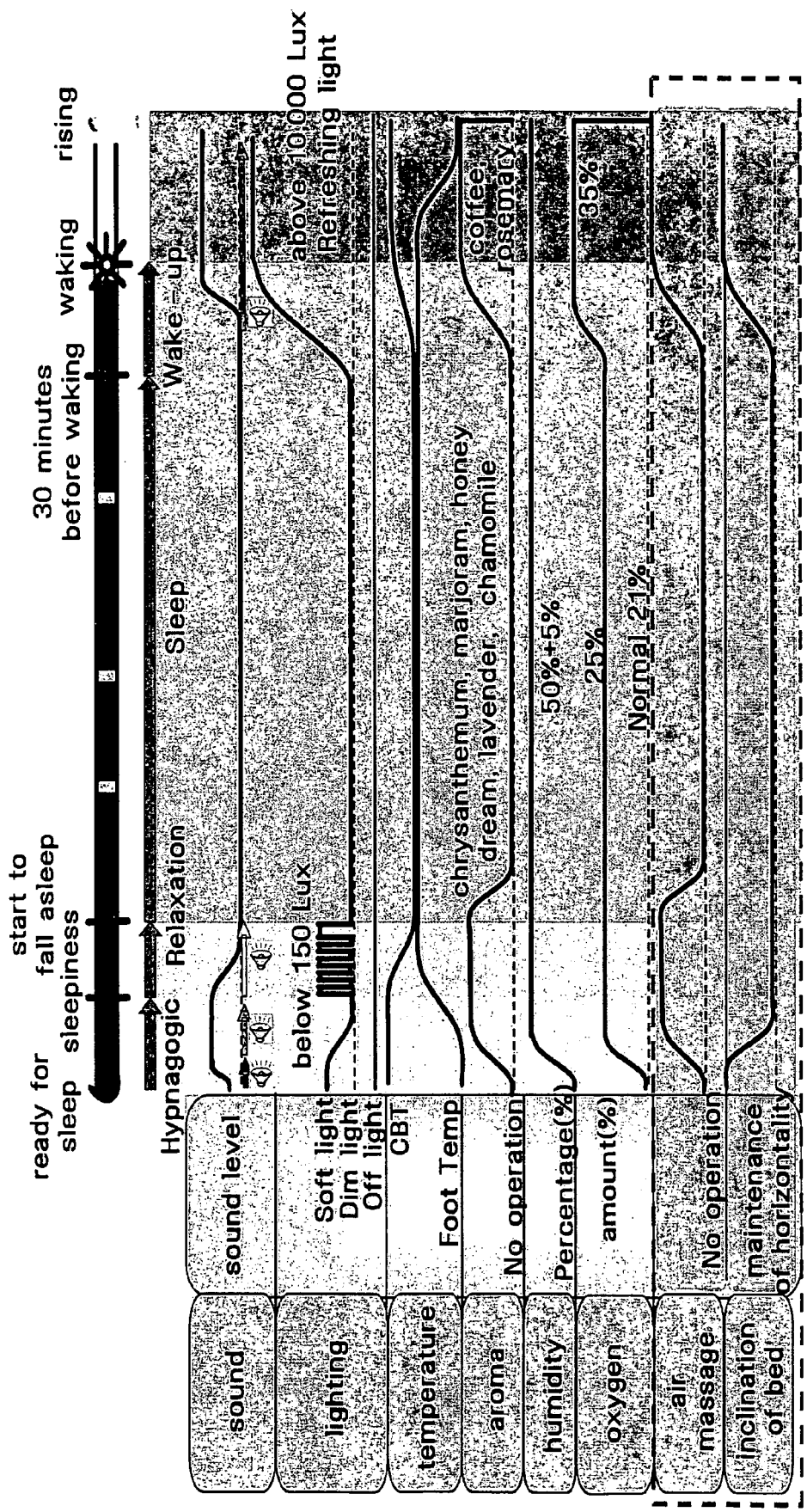
FIG. 7 is a diagram illustrating a method of adjusting the sleep environment for each of the sleep stages as a graph in the method of inducing sound sleep and waking according to the embodiment of the present invention.

FIG. 6 is a diagram illustrating a method of adjusting the sleep environment for each sleep stage as a table in the method of inducing sound sleep and waking according to the embodiment of the present invention, and FIG. 7 is a diagram illustrating the method of adjusting the sleep environment for each sleep stage as a graph.

As described above, sleep stages include, as illustrated in FIG. 5, a total of four stages: a hypnagogic stage spanning from lying in bed to immediately before feeling sleepy, a relaxation stage spanning from feeling sleepy to immediately before completely falling asleep, a sleep stage spanning from completely falling asleep to immediately before finally inducing waking, and a wake-up stage spanning from starting to wake up to finally waking up.

Referring to FIGS. 6 and 7, with the case of sound effects in a silent environment, peaceful music is output in the hypnagogic stage, the sound level of the music gradually decreases in the relaxation stage, the sound disappears in the sleep stage, and peaceful music is again output in the wake-up stage. Furthermore, when light is taken as an example, soft and gentle light becomes gradually dark from below 150 lux of illumination in the hypnagogic stage, the light flickers four times at a constant interval and once at a long interval to induce deep breathing in the relaxation stage, the light is kept dim in the sleep stage. Thereafter, in the wake-up stage, ambient light gradually becomes bright again using indirect lighting and, when the wake-up time is reached, the light from natural light and a fluorescent lamp is kept at 1000 lux of illumination. In addition, the sleep environment can be adjusted using the operation of an air massage device. The intensity of air massage gradually increases in the hypnagogic stage, the intensity gradually decreases in the relaxation stage, the state is maintained such that there is no action of the massage in the sleep stage, and finally the intensity of the massage again increases in the wake-up stage. In the case of the inclination of a bed, the inclination become lower in the hypnagogic stage, the inclination is maintained horizontal in the relaxation stage, and the inclination again becomes higher in the wake-up stage. Similarly, in the case of oxygen, the amount of oxygen gradually increases in the hypnagogic stage, the amount of oxygen is maintained at 25% in the relaxation stage, and the amount of oxygen increases in the wake-up stage. In the case of humidity, the amount of humidity gradually increases in the hypnagogic stage, and then be continuously maintained at a constant value according to an aspect of the present invention.

With respect to temperature and aroma, a principle similar to that illustrated in FIGS. 6 and 7 is applied, and, therefore, descriptions thereof are omitted.

Meanwhile, it is understood the scope of the present invention may be applied to a computer program product executable by a computer, which includes operations of performing the above-described methods.

The apparatus and method of inducing sound sleep and waking of the present invention measure the physiological signals of a user using a sensor which does not contact the body of a user, and, at the same time, control the sleep environment, thereby applying this to the sleep environment and enabling feedback control to induce sound sleep and waking. As a result, there is an advantage in that it is possible to naturally induce sound sleep and waking.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An apparatus to induce sound sleep and waking, comprising:
   an input unit to receive a sleep type from a user;
   a protocol selection unit to select a protocol to control an environment for sound sleep and waking depending on the received sleep type;
   a sleep environment adjustment unit to adjust a sleep environment of the user according to the selected protocol;
   a sleep state determination unit to determine a sleep state of the user by measuring simultaneously a plurality of physiological signals of the user measured through indicators during sleep in the sleep environment using one sensor that does not contact a body of the user and detects frequency variation depending on location of the user; and
   a physiological signal variation detection unit to detect a variation in the physiological signals of the user using the determined sleep state;
   wherein, when the variation in the physiological signals is detected by the physiological signal variation detection unit, the sleep environment adjustment unit re-adjusts the sleep environment by changing one or more parameters of the protocol depending on the variation,
   wherein the physiological signal variation detection unit detects variation in the physiological signals of the user by comparing at least one of increases, decreases, and lacks of change of the indicators with those of a physiological signal variation model corresponding to a determined sleep stage from among sleep stages of the user, the sleep stages including a hypnagogic stage spanning from lying in bed to immediately before feeling sleepy, a relaxation stage spanning from feeling sleepy to immediately before falling asleep, a sleep stage spanning from falling asleep to immediately before finally inducing waking, and a wake-up stage spanning from starting to wake up to finally waking up, and
   wherein adjusting the sleep environment includes adjusting inclination of a bed from an initial inclined position, the inclination becoming lower in the hypnagogic stage, the inclination being maintained horizontal in the relaxation stage and sleep stage, and the inclination again becoming higher in the wake-up stage, and
   adjusting a light in the sleep environment, the light being gradually being darkened in the hypnagogic stage, the light flickering four times at a constant interval and once at a longer interval than said constant interval to induce deep breathing in the relaxation stage, the light being kept dim in the sleep stage, and the light being gradually brightened in the wake-up stage.

2. The apparatus of claim 1, wherein the input unit receives a wake-up time with respect to a sleep onset time of the user and calculates a sleep time and total sleep duration.

3. The apparatus of claim 1, wherein the parameters of the protocol comprise levels representing content, including sound and image information and information about states of an external environment of a sleep space, the levels being adjusted by at least one of oxygen, humidity, and aroma for each of the sleep stages of sleep duration from a sleep onset time to a wake-up time.

4. The apparatus of claim 3, wherein the indicators include heart rate, heart rate variability and respiratory rate derived from heartbeat and respiration.

5. The apparatus of claim 4, wherein the sleep state is determined based on whether the indicators increase, decrease or maintain.

6. The apparatus of claim 1, wherein the sensor is a Doppler radar sensor located within a distance of about three meters from the heart of the user.

7. The apparatus of claim 1, wherein the sleep state determination unit determines the sleep state by measuring behavior of the user during sleep.

8. The apparatus of claim 1, wherein the sleep environment adjustment unit adjusts the sleep environment of the user by controlling one or more of an oxygen generation device, a humidity control device, and a aroma generation device.

9. A method of inducing sound sleep and waking, comprising:
  selecting a protocol to control a sound sleep and waking environment depending on a sleep type selected by a user;
  adjusting the sleep environment of the user according to the selected protocol;
  determining a sleep state of the user by measuring simultaneously, measured through indicators, a plurality of physiological signals of the user during sleep in the sleep environment using one sensor which does not contact a body of the user and detects frequency variation depending on location of the user;
  detecting variation in the physiological signals of the user comprising at least one of comparing lacks of change, increases, and decreases of the indicators with those of a physiological signal variation model corresponding to a sleep stage of the user determined from among a plurality of sleep stages, the plurality of sleep stages including a hypnagogic stage spanning from lying in bed to immediately before feeling sleepy, a relaxation stage spanning from feeling sleepy to immediately before falling asleep, a sleep stage spanning from falling asleep to immediately before finally inducing waking, and a wake-up stage spanning from starting to wake up to finally waking up; and
  re-adjusting the sleep environment by changing parameters of the protocol depending on the detected variation in the physiological signals,
  wherein re-adjusting the sleep environment includes
    adjusting inclination of a bed from an initial inclined position, the inclination becoming lower in the hypnagogic stage, the inclination being maintained horizontal in the relaxation stage and sleep stage, and the inclination again becoming higher in the wake-up stage, and
    adjusting a light in the sleep environment, the light being gradually being darkened in the hypnagogic stage, the light flickering four times at a constant interval and once at a longer interval than said constant interval to induce deep breathing in the relaxation stage, the light being kept dim in the sleep stage, and the light being gradually brightened in the wake-up stage.

10. The method of claim 9, wherein the selecting operation comprises receiving a wake-up time with respect to a sleep onset time of the user, and calculating a sleep time and total sleep duration, thus selecting a sleep type.

11. The method of claim 9, wherein the parameters of the protocol comprise levels content, including sound and images, and information about states of an external environment of a sleep space, the levels being adjusted through at least one of oxygen, humidity, and aroma for each of the sleep stages from a sleep onset time to a wake-up time.

12. The method of claim 9, wherein the indicators include heart rate, heart rate variability and respiratory rate derived from heartbeat and respiration.

13. The method of claim 12, wherein the sleep state is determined based on whether the indicators increase, decrease or maintain.

14. The method of claim 9, wherein the sensor is a Doppler radar sensor located within a distance of about three meters from a heart of the user.

15. The method of claim 9, wherein the determining a sleep state of the user comprises determining the sleep state by measuring behavior of the user during sleep.

16. The method of claim 9, wherein the adjusting comprises adjusting the sleep environment of the user by controlling one or more of an oxygen generation device, a humidity control device, and an aroma generation device.

17. A non-transitory computer-readable recording medium for controlling a computer and having embedded thereon a computer program, said computer program performing:
  selecting a protocol to control a sound sleep and waking environment depending on a sleep type selected by a user;
  adjusting the sleep environment of the user according to the selected protocol;
  determining a sleep state of the user by measuring simultaneously, using indicators, a plurality of physiological signals of the user during sleep in the sleep environment using one sensor which does not contact a body of the user and detects frequency variation depending on location of the user;
  detecting variation in the physiological signals of the user comprising comparing at least one of increases, decreases, and lacks of change of the indicators with those of a physiological signal variation model corresponding to a determined sleep stage of the user, the sleep stages including a hypnagogic stage spanning from lying in bed to immediately before feeling sleepy, a relaxation stage spanning from feeling sleepy to immediately before falling asleep, a sleep stage spanning from falling asleep to immediately before finally inducing waking, and a wake-up stage spanning from starting to wake up to finally waking up; and
  re-adjusting the sleep environment by changing parameters of the protocol depending on the detected variation in the physiological signals,
  wherein re-adjusting the sleep environment includes
    adjusting inclination of a bed from an initial inclined position, the inclination becoming lower in the hypnagogic stage and sleep stage, the inclination being maintained horizontal in the relaxation stage, and the inclination again becoming higher in the wake-up stage, and adjusting a light in the sleep environment, the light being gradually being darkened in the hypnagogic stage, the light flickering four times at a constant interval and once at a longer interval than said constant interval to induce deep breathing in the relaxation stage, the light being kept dim in the sleep stage, and the light being gradually brightened in the wake-up stage.

* * * * *